United States Patent
Karpinski et al.

(10) Patent No.: US 8,865,897 B2
(45) Date of Patent: Oct. 21, 2014

(54) CRYSTAL MODIFICATIONS-3-(1H-INDOL-3-YL)-4-[4-METHYL-PIPERAZIN-1-YL)-QUINAZOLIN-4-YL]-PYRROLE-2, 5-DIONE

(75) Inventors: Piotr Karpinski, Lincoln Park, NJ (US); Stéphanie Monnier, Raedersheim (FR); Elias Ndzie, Basel (CH); Dimitris Papoutsakis, Action, MA (US); Paul A Sutton, Parsippany, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/445,371

(22) PCT Filed: Oct. 18, 2007

(86) PCT No.: PCT/US2007/022241
§ 371 (c)(1), (2), (4) Date: Apr. 13, 2009

(87) PCT Pub. No.: WO2008/051440
PCT Pub. Date: May 2, 2008

(65) Prior Publication Data
US 2010/0041884 A1    Feb. 18, 2010

Related U.S. Application Data

(60) Provisional application No. 60/853,384, filed on Oct. 20, 2006.

(51) Int. Cl.
*C07D 403/14*    (2006.01)
(52) U.S. Cl.
CPC .................. *C07D 403/14* (2013.01)
USPC ...................................... 544/284
(58) Field of Classification Search
CPC .................................. C07D 403/14
USPC .......................................... 544/284
See application file for complete search history.

(56) References Cited

FOREIGN PATENT DOCUMENTS

WO    WO 02/38561    5/2002
WO    2008155022 A1    12/2008

OTHER PUBLICATIONS

Mino Caira, "Crystalline Polymorphism of Organic Compounds", Topics in Current Chemistry, Springer, Berlin, DE, vol. 198, 1998, pp. 163-208, (XP001156954).

*Primary Examiner* — Brian McDowell
(74) *Attorney, Agent, or Firm* — Jennifer Chapman (57) ABSTRACT

The invention relates to a new crystalline form of the acetate salt of

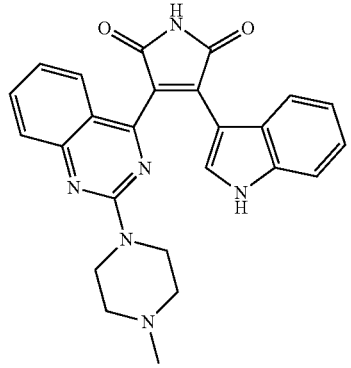

which may be used, for example, for prevention or treatment of transplant rejection.

9 Claims, 11 Drawing Sheets

Fig. 1 : X-ray Powder Diffraction Diagram of Form A

Fig. 2 : FT-IR spectrum of Form A

Fig. 3: FT-Raman spectrum of Form A.

Fig 4: SEM picture of Form A.

Fig. 5: X-ray diffraction diagram of form B

Fig. 6: FT-IR spectrum of Form B

Fig. 7 : FT-Raman spectrum of Form B.

Fig. 8: SEM picture of Form B.

Fig. 9: X-ray powder diffraction pattern of amorphous form.

Fig 10: FT-IR Spectrum of amorphous form

Fig 11: FT-RAMAN Spectrum of amorphous form

CRYSTAL MODIFICATIONS-3-(1H-INDOL-3-YL)-4-[4-METHYL-PIPERAZIN-1-YL)-QUINAZOLIN-4-YL] -PYRROLE-2, 5-D IONE

This application is a 371 of PCT/US2007/022241, filed Oct. 18, 2007 and claims benefit of U.S. Provisional Application 60/1853,384, filed Oct. 20, 2006. The contents of the above applications is incorporated herein in their entirety.

The present invention relates to particular forms of the acetate salt of 3-(1.H.-indol-3-yl)-4-[2-(4-methyl-piperazin-1-yl)-quinazolin-4-yl]-pyrrole-2,5-dione, comprising amorphous form and certain crystals, processes for the preparation thereof, pharmaceutical compositions containing such amorphous and crystal form, and their use in diagnostic methods or preferably for the therapeutic treatment of warm-blooded animals, especially humans, or their use for the preparation of pharmaceutical preparations for use in diagnostic methods or preferably for the therapeutic treatment of warm-blooded animals, especially humans.

3-(1.H.-indol-3-yl)-4-[2-(4-methyl-piperazin-1-yl)-quinazolin-4-yl]-pyrrole-2,5-dione can be represented by the following formula and is known from WO2002/38561 (example 56), the entire disclosure of which is incorporated by reference, and can be synthesized as described therein.

It has now been surprisingly found that amorphous form, crystal forms, e.g. polymorphs, or pseudopolymorphs, such as solvates of hydrates, may under certain conditions be found in the acetate salt of this compound, which are described hereinafter e.g. as A, B, C or D crystal forms or the solvate form $S_A$, and which have very advantageous properties. Such forms show improved stability and purity and thus e.g. easier handling in plant and open up new possibilities for improved formulation of pharmaceutical compositions for 3-(1.H.-indol-3-yl)-4-[2-(4-methyl-piperazin-1-yl)-quinazolin-4-yl]-pyrrole-2,5-dione acetate, such as e.g. high dose formulations.

For the purpose of the present invention, the term "crystal of the invention" encompasses the amorphous form, crystal forms, e.g. polymorphs, and pseudo-polymorphs, e.g. solvate and hydrate, of the 3-(1.H.-indol-3-yl)-4-[2-(4-methyl-piperazin-1-yl)-quinazolin-4-yl]-pyrrole-2,5-dione acetate. Examples of crystal of the invention are form A, form B, form C, form D, and form $S_A$.

The present invention provides a amorphous form, crystal forms, e.g. polymorphs, and pseudo-polymorphs, e.g. solvate and hydrate, of the 3-(1.H.-indol-3-yl)-4-[2-(4-methyl-piperazin-1-yl)-quinazolin-4-yl]-pyrrole-2,5-dione acetate, in particular the form A, B, as defined herebelow, the form $S_A$, or mixture thereof, preferably form B or mixture of form A and B.

The amorphous and crystalline forms of 3-(1.H.-indol-3-yl)-4-[2-(4-methyl-piperazin-1-yl)-quinazolin-4-yl]-pyrrole-2,5-dione acetate are preferably essentially pure. The term essentially pure in accordance with the present invention is means that the sum of related substances is less than 1%, preferably less than 0.75%, more preferably less than 0.5% and that the residual solvents and water are less than 1%, preferably less than 0.75%, more preferably less than 0.5% and still more preferably less than 0.25% by weight.

In another preferred embodiment the crystalline form of 3-(1.H.-indol-3-yl)-4-[2-(4-methyl-piperazin-1-yl)-quinazolin-4-yl]-pyrrole-2,5-dione acetate is not hydrated, i.e. the anhydrate. The anhydrate can e.g. be prepared by dehydration of the monohydrate under suitable conditions.

In another preferred embodiment of the invention, there is provided a crystalline form of 3-(1.H.-indol-3-yl)-4-[2-(4-methyl-piperazin-1-yl)-quinazolin-4-yl]-pyrrole-2,5-dione acetate, e.g. form A or B, which is anhydrous.

In yet another preferred embodiment of the invention, there is provided a solvate of 3-(1.H.-indol-3-yl)-4-[2-(4-methyl-piperazin-1-yl)-quinazolin-4-yl]-pyrrole-2,5-dione acetate, e.g. obtained in solvent such as acetone, ethanol, tertahydrofrurane, acetonitrile, methanol or water (hydrate). In particular the present invention provides the hydrate form of 3-(1.H.-indol-3-yl)-4-[2-(4-methyl-piperazin-1-yl)-quinazolin-4-yl]-pyrrole-2,5-dione acetate is a solvate, e.g. monohydrate form.

In another preferred embodiment of the invention, there is provided a crystalline form of 3-(1.H.-indol-3-yl)-4-[2-(4-methyl-piperazin-1-yl)-quinazolin-4-yl]-pyrrole-2,5-dione acetate, e.g. the crystal form A, B, C or D, as hereinbelow described, or mixture thereof.

FIGURES

FIG. 2 shows the FT-IR spectrum of Form A. FT-IR spectrum is recorded in Nujol mull between 2 KBr plates using a Bruker Vertex. The sample is tested as is using ATR (attenuated total reflectance) sampling device.

FIG. 6 shows the FT-IR spectrum of Form B. FT-IR spectrum is recorded in Nujol mull between 2 KBr plates using a Bruker Vertex. The sample is tested as is using ATR (attentenous total reflectance) sampling device.

FORM B

Form B is slightly hygroscopic with maximum water uptake of 0.7% at 80% r.h.

TABLE 1

| Relative humidity % | Moisture Sorption at 25° |
|---|---|
| 45 | 0.4 |
| 55 | 0.5 |
| 75 | 0.6 |
| 85 | 0.7 |
| 95 | 0.6 |
| hygroscopic | slightly |
| XRPD pattern after DVS | no change |

Differential Scanning Calorimery (DSC): the melting onset temperature of form B is about 220° C., e.g. about 190° C.

Figure 1:
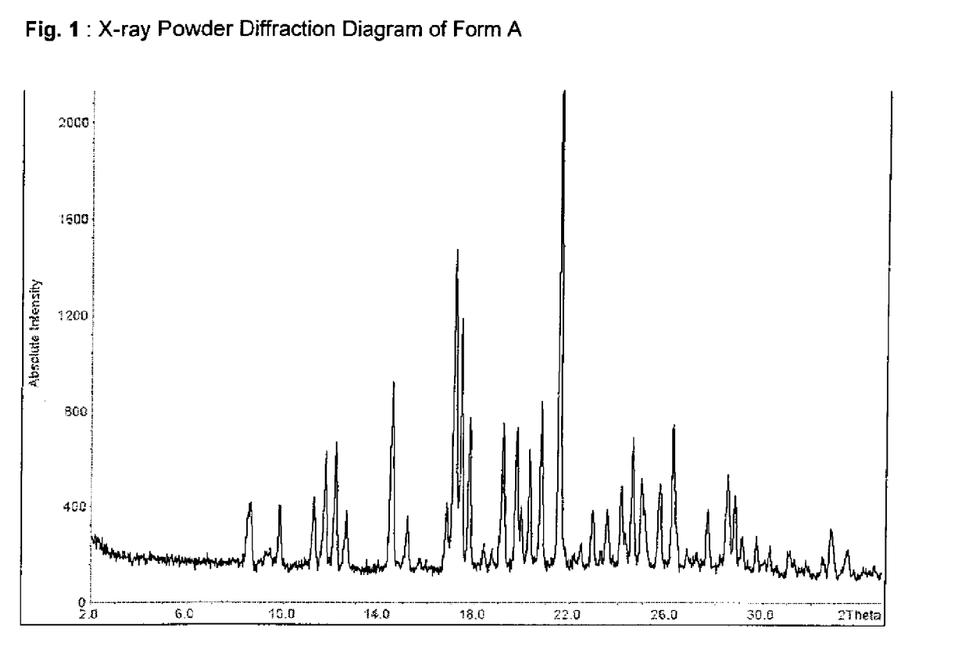
FIG. 1 shows the X-ray Powder Diffraction Diagram of Form A of the acetate anhydrate salt of 3-(1.H.-indol-3-yl)-4-[2-(4-methyl-piperazin-1-yl)-quinazolin-4-yl]-pyrrole-2,5-dione. X-ray powder diffraction patterns are measured using a Bruker STOE instrument with CuK alpha radiation source.
Figure 2:
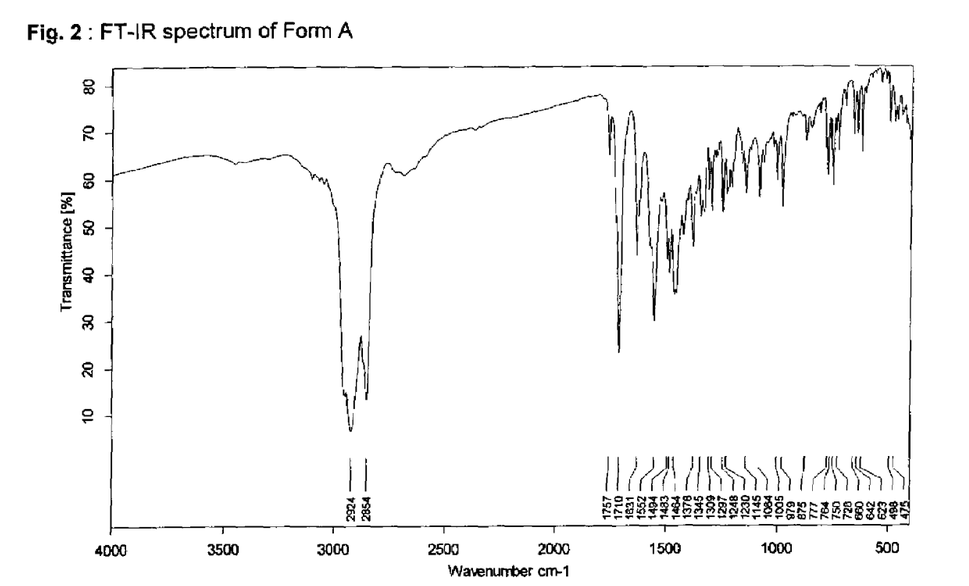
Figure 3:
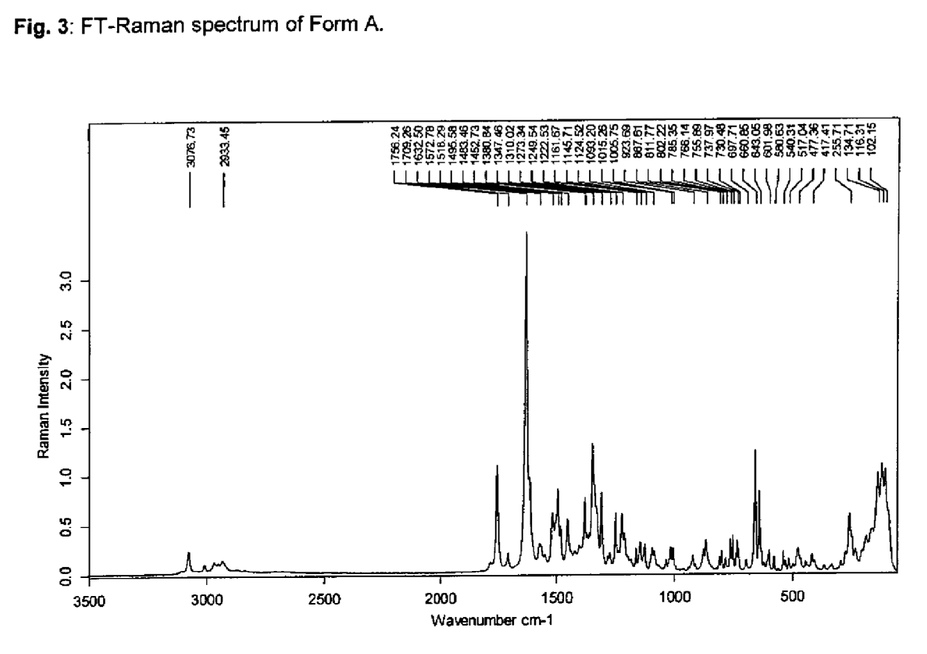
FIG. 3 shows the FT-Raman spectrum of Form A. The FT-Raman spectrum is recorded using a Bruker RFS 100 instrument.

The X-ray diffraction pattern depicted in FIG. 1 for Form B is summarized in Table 2 which lists most significant diffraction peaks.

The XRPD (X-ray Powder Diffraction) shows a strong diffraction peak at an angle of about 9.7° 2theta.

TABLE 2

| 2-theta (deg) | d-spacings (A) | Relative intensity |
|---|---|---|
| 8.4 | 10.50 | Low |
| 9.7 | 9.07 | Strong |
| 13.9 | 6.35 | Low |
| 16.8 | 5.24 | Low |
| 17.3 | 5.11 | Low |
| 18.8 | 4.71 | Low |
| 19.0 | 4.66 | Low |
| 19.9 | 4.45 | Medium |
| 20.5 | 4.31 | Medium |
| 25.9 | 3.42 | Medium |
| 27.1 | 3.28 | Medium |
| 27.4 | 3.24 | Low |
| 27.8 | 3.20 | Low |
| 28.2 | 3.15 | Low |
| 35.0 | 2.56 | Strong |

Form B may be characterized by the following major IR bands: Main IR bands: 1754; 1711; 1574; 1486; 1462; 1378; 1248; 1086; 976; 770; 723; 661; 622 cm$^{-1}$.

Form B may be characterized by the following main RAMAN bands: 3064; 1754; 1711; 1625; 1574; 1485; 1445; 1388; 1334; 1309; 1246; 1212; 664; 645 cm$^{-1}$ Form B is orange.

Form A

The melting onset temperature of form A is about 180° C., e.g. 182° C.

Figure 4:
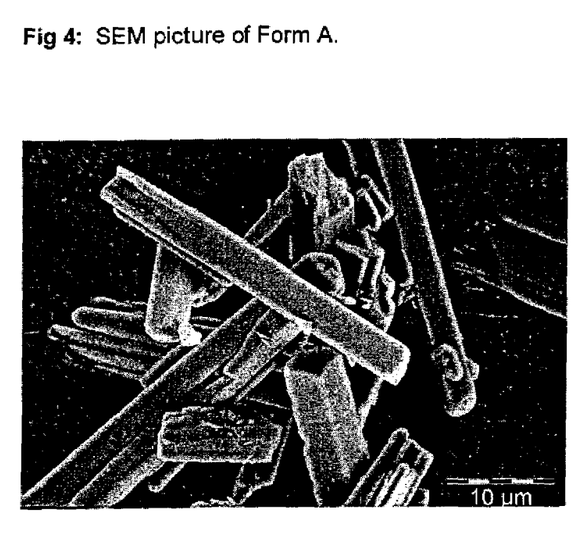
FIG. 4 shows a microscopic view of Form A.
Figure 5:
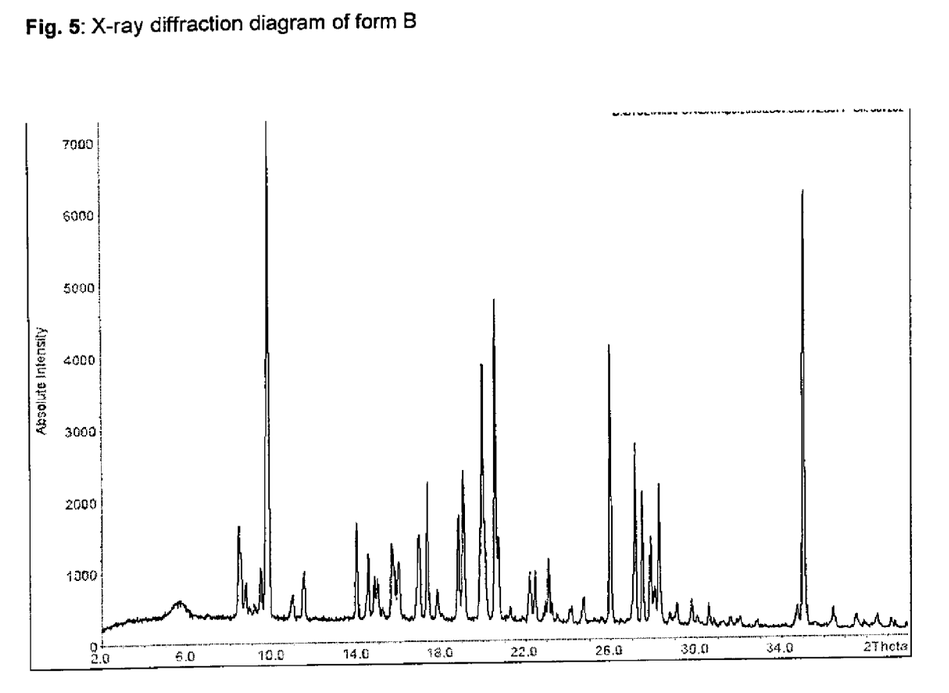
FIG. 5 shows the X-ray diffraction diagram of form B of the acetate anhydrate salt of 3-(1.H.-indol-3-yl)-4-[2-(4-methyl-piperazin-1-yl)-quinazolin-4-yl]-pyrrole-2,5-dione. In the X-ray diagram, the angle of diffraction is plotted on the horizontal axis (x-axis) and the peak intensity on the vertical (y-axis). X-ray powder diffraction patterns are measured using a Bruker STOE instrument with CuK alpha radiation source).
Figure 6:
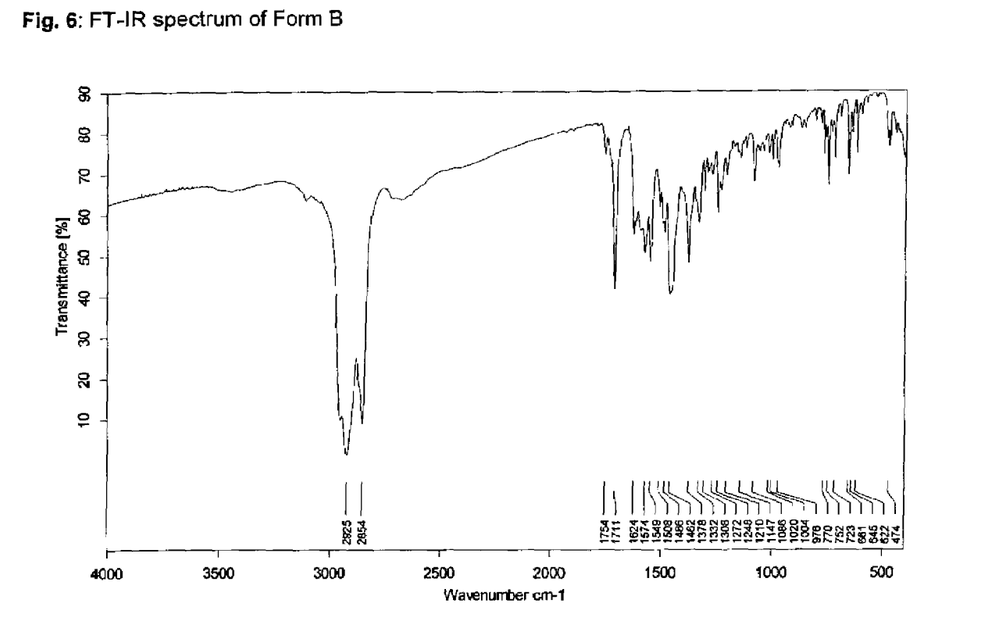
Figure 7:
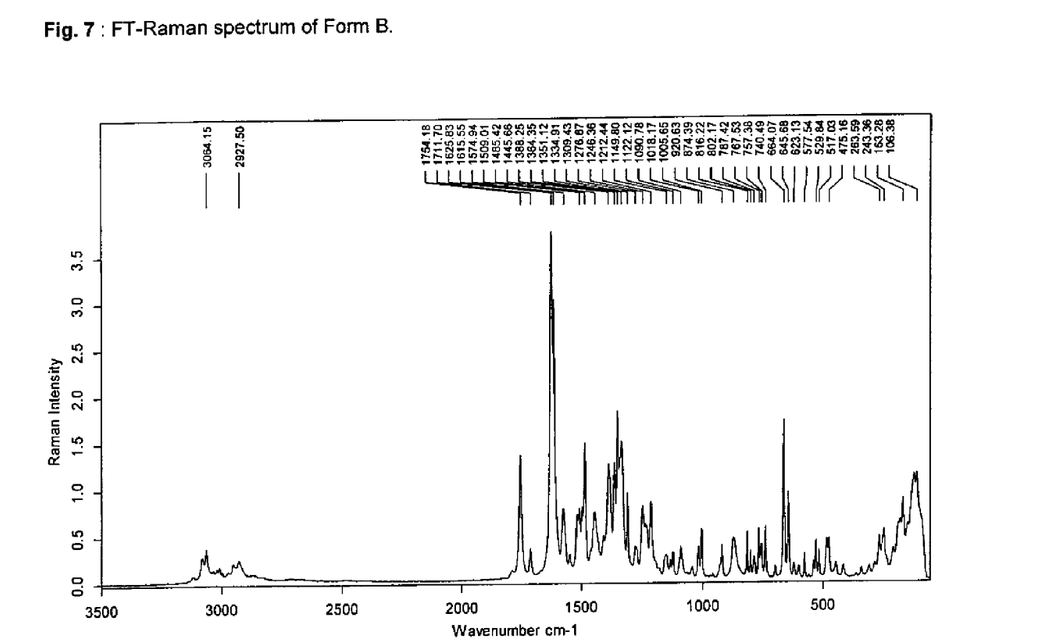
FIG. 7 shows the FT-Raman spectrum of Form B. The FT-Raman spectrum is recorded using a Bruker RFS 100 instrument.
Figure 8:
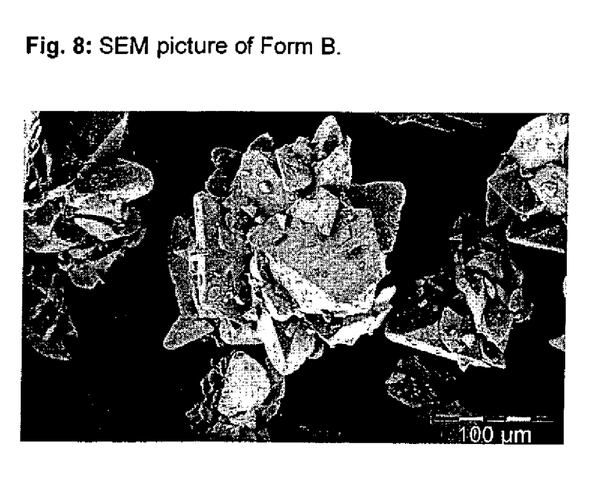
FIG. 8 shows a microscopic view of Form B.
Figure 9:
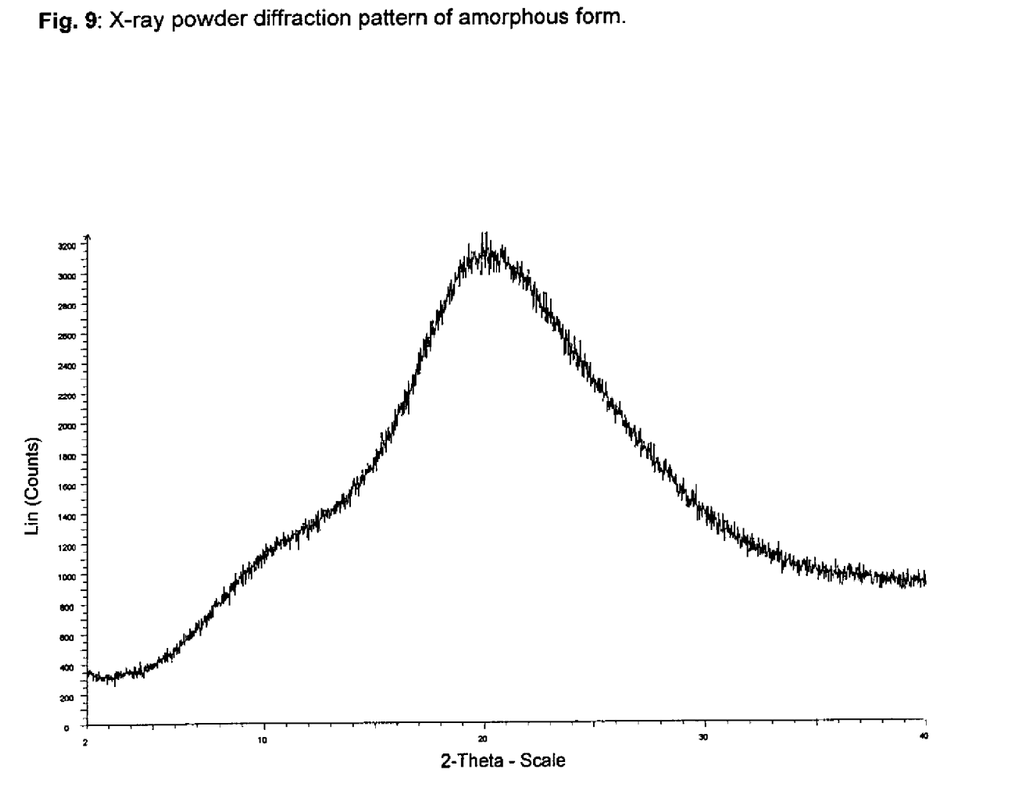
FIG. 9 shows a X-ray powder diffraction pattern of amorphous form.
Figure 10:
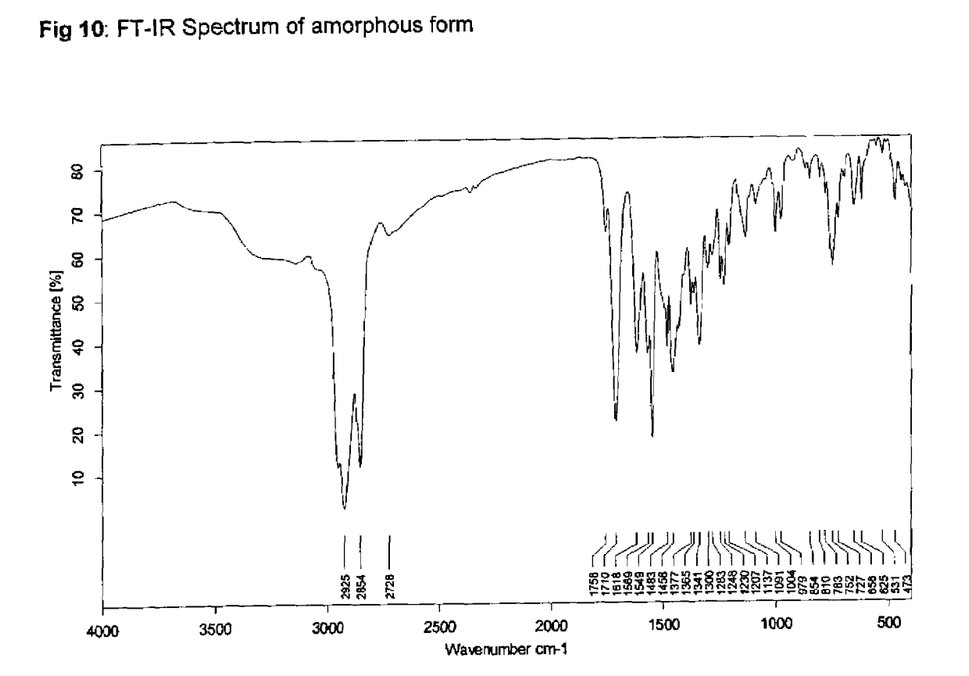
FIG. 10 shows a FT-IR Spectrum of amorphous form.
Figure 11:
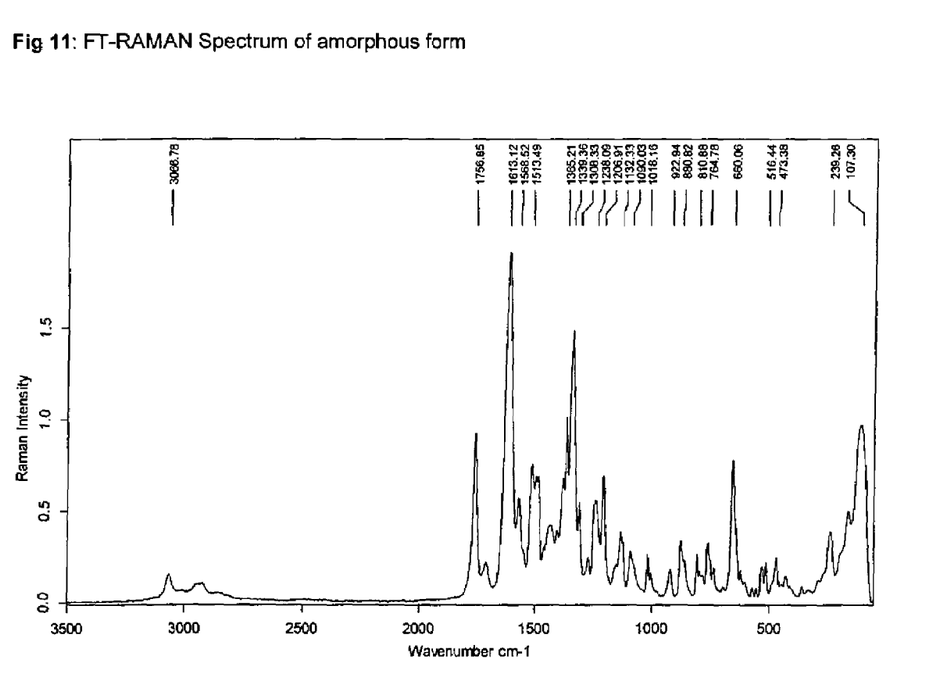
FIG. 11 shows a FT-RAMAN Spectrum of amorphous form.

The X-ray diffraction pattern depicted in FIG. 4 for Form A is summarized in Table 3. The XRPD shows a strong diffraction peak at about 21.5° 2 Theta, e.g. 21.4° 2 Theta.

TABLE 3

| 2-theta (deg) | d-spacings (A) | Relative intensity |
|---|---|---|
| 8.5 | 10.28 | Low |
| 11.2 | 7.87 | Low |
| 11.6 | 7.56 | Medium |
| 12.1 | 7.27 | Medium |
| 12.6 | 7.01 | Low |
| 14.5 | 6.09 | Strong |
| 17.1 | 5.17 | Strong |
| 17.3 | 5.14 | Strong |
| 17.7 | 4.97 | Strong |
| 19.2 | 4.61 | Medium |
| 19.7 | 4.48 | Medium |
| 20.3 | 4.36 | Medium |
| 20.8 | 4.26 | Medium |
| 21.5 | 4.11 | Strong |
| 22.9 | 3.87 | Low |
| 24.6 | 3.61 | Low |
| 24.9 | 3.55 | Low |
| 26.2 | 3.38 | Medium |
| 34.7 | 2.57 | Medium |

Form A may be distinguished from form B in particular by at least one of the following XRPD diffraction peaks: about 11.6°, about 12.0° and about 21.5° 2 Theta.

Form A may be characterized by the following major IR bands: 1757; 1710; 1631; 1552; 1378; 1145; 1084; 1005; 979; 777; 750; 660; 642; 623 cm$^{-1}$.

Form A may be characterized by the following main RAMAN bands: 3076; 1756; 1632; 151; 1495; 1380; 1347; 1310; 1249; 1222; 660; 643; 255 cm$^{-1}$.

Form A is yellow.

In one preferred embodiment there is provided a crystalline form exhibiting at least one of the following major IR bands: 1711; 1574; 1486; 1462; 1378; 1248; 1086; 976; 770; 723; 661; 622 cm$^{-1}$.

In another preferred embodiment there is provided a crystalline form exhibiting at least one of the following main RAMAN bands: 3064; 1754; 1711; 1625; 1574; 1485, 1445; 1388; 1334; 1309; 1246; 1212; 664; 645 cm$^{-1}$.

In yet another preferred embodiment there is provided a crystalline form exhibiting at least one of the following major IR bands: 1757; 1710; 1631; 1552; 1378; 1145; 1084; 1005; 979; 777; 750, 660; 642; 623 cm$^{-1}$.

In a further preferred embodiment there is provided a crystalline form exhibiting at least one of the following main RAMAN bands: 3076; 1756; 1632; 151; 1495; 1380; 1347; 1310; 1249; 1222; 660; 643; 255 cm$^{-1}$.

Amorphous

The melting onset temperature of amorphous form is comprised between about 100 and about 110° C.

Amorphous form of 3-(1.H.-indol-3-yl)-4-[2-(4-methyl-piperazin-1-yl)-quinazolin-4-yl]-pyrrole-2,5-dione acetate is orange.

Form C

X-Ray Diffraction Pattern:

| Caption Legend Angle 2-Theta° | d value Angstrom | Intensity | Intensity % Count % | |
|---|---|---|---|---|
| d = 11.12392 | 7.941 | 11.12392 | 18.5 | 25.2 |
| d = 7.30123 | 12.112 | 7.30123 | 55.9 | 76.0 |
| d = 6.72964 | 13.145 | 6.72964 | 72.4 | 98.4 |
| d = 5.56453 | 15.914 | 5.56453 | 73.5 | 100.0 |
| d = 4.50771 | 19.678 | 4.50771 | 27.9 | 38.0 |
| d = 3.71260 | 23.949 | 3.71260 | 27.5 | 37.4 |
| d = 3.36244 | 26.486 | 3.36244 | 18.4 | 25.0 |
| d = 3.08551 | 28.913 | 3.08551 | 17.8 | 24.1 |

-continued

| Caption Legend Angle 2-Theta° | d value Angstrom | Intensity | Intensity % Count % | |
|---|---|---|---|---|
| d = 5.89980 | 15.004 | 5.89980 | 14.3 | 19.4 |
| d = 4.33943 | 20.449 | 4.33943 | 18.6 | 25.3 |

Form D
X-Ray Diffraction Pattern:

| Caption Legend Angle 2-Theta° | d value Angstrom | Intensity | Intensity % Count % | |
|---|---|---|---|---|
| d = 12.57863 | .022 | 12.57863 | 13.3 | 21.1 |
| d = 9.38691 | .414 | 9.38691 | 7.89 | 12.5 |
| d = 7.56740 | 1.684 | 7.56740 | 38.6 | 61.0 |
| d = 7.00101 | 2.633 | 7.00101 | 38.3 | 60.6 |
| d = 6.52871 | 3.551 | 6.52871 | 41.7 | 66.1 |
| d = 6.19280 | 4.290 | 6.19280 | 15.9 | 25.2 |
| d = 5.65533 | 5.657 | 5.65533 | 15.7 | 24.8 |
| d = 5.43397 | 6.299 | 5.43397 | 16.5 | 26.1 |
| d = 4.90500 | 8.070 | 4.90500 | 36.9 | 58.3 |
| d = 4.82526 | 8.371 | 4.82526 | 37.4 | 59.1 |
| d = 4.61467 | 9.218 | 4.61467 | 46.7 | 73.8 |
| d = 4.38054 | 0.255 | 4.38054 | 15.6 | 24.7 |
| d = 4.19701 | 1.151 | 4.19701 | 35.0 | 55.4 |
| d = 4.08436 | 1.741 | 4.08436 | 63.2 | 100.0 |
| d = 3.92054 | 2.662 | 3.92054 | 27.1 | 42.9 |
| d = 3.84973 | 3.084 | 3.84973 | 18.6 | 29.4 |
| d = 3.78031 | 3.514 | 3.78031 | 18.2 | 28.8 |
| d = 3.57714 | 4.870 | 3.57714 | 20.4 | 32.3 |
| d = 3.36272 | 6.484 | 3.36272 | 21.3 | 33.7 |
| d = 3.23975 | 7.509 | 3.23975 | 24.2 | 38.3 |
| d = 3.18739 | 7.970 | 3.18739 | 17.1 | 27.1 |
| d = 3.14160 | 8.386 | 3.14160 | 19.9 | 31.5 |
| d = 2.89173 | 0.897 | 2.89173 | 15.6 | 24.7 |
| d = 2.52207 | 5.566 | 2.52207 | 12.7 | 20.1 |
| d = 2.40324 | 37.388 | 2.40324 | 10.5 | 16.7 |
| d = 8.44175 | 10.471 | 8.44175 | 10.7 | 16.9 |
| d = 8.18454 | 10.801 | 8.18454 | 10.0 | 15.9 |
| d = 3.51031 | 25.352 | 3.51031 | 24.7 | 39.1 |

The invention also includes a process for the preparation of the crystals of the invention which comprises the step of forming a solution of 3-(1.H.-indol-3-yl)-4-[2-(4-methyl-piperazin-1-yl)-quinazolin-4-yl]-pyrrole-2,5-dione acetate and crystallizing the acetate from solution by precipitation or recrystallization. In particular, the process for the preparation of the crystals of the invention comprises the step of reacting 3-(1.H.-indol-3-yl)-4-[2-(4-methyl-piperazin-1-yl)-quinazolin-4-yl]-pyrrole-2,5-dione in free base form with acetic acid and recovering from the reaction mixture the resultant salt, and the step of reacting an appropriate inert solvent such as acetone, acetonitrile, ethanol, ethyl acetate, heptane, t-butyl methyl ether, methylene chloride, 2-propanol, i-propyl acetate, toluene, E95, or a mixture EtAC/ethanol, e.g. 75/25 vol % or 50/50 vol %. Preferred solvent is acetone.

In accordance with the present invention a process for the crystallization of 3-(1.H.-indol-3-yl)-4-[2-(4-methyl-piperazin-1-yl)-quinazolin-4-yl]-pyrrole-2,5-dione acetate is provided. The precise conditions under which crystals are formed may now be empirically determined and a number of methods are suitable in practice, including the crystallization conditions as described in Examples 1 to 8.

Crystallization-inducing conditions normally involve the use of an appropriate crystallization-inducing solvent, such as acetone, acetonitrile, ethanol, ethyl acetate, heptane, or t-butyl methyl ether, methylene chloride, 2-propanol, i-propyl acetate, toluene, E95 or a mixture EtAC/ethanol, e.g. 75/25 vol % or 50/50 vol %. Preferred solvents are ethyl acetate, heptane, t-butyl methyl ether, methylene chloride, 2-propanol, i-propyl acetate, toluene, and mixture EtAC/ethanol, e.g. 75/25 vol % or 50/50 vol % Conveniently, 3-(1.H.-indol-3-yl)-4-[2-(4-methyl-piperazin-1-yl)-quinazolin-4-yl]-pyrrole-2,5-dione is dissolved in the solvent at ambient temperature. The solution may be produced by dissolving in a solvent any one or more of amorphous forms of 3-(1.H.-indol-3-yl)-4-[2-(4-methyl-piperazin-1-yl)-quinazolin-4-yl]-pyrrole-2,5-dione, and solvates thereof, such as hydrate. Crystals may then be formed by conversion from free base to the salt, crystallization taking place at a temperature of between about 0° C. as above and 40° C., preferably at ambient temperature.

The dissolution and crystallization may be carried out in various conventional ways. For instance, free base may be dissolved in a solvent or a mixture of solvents in which it is readily soluble at ambient temperatures but in which it acetate salt is only sparingly soluble at the same temperatures. Dissolution of the free base at elevated temperature followed by cooling after salt formation can also help the acetate salt crystals crystallize out of solution. Mixed solvents comprising a good solvent in which 3-(1.H.-indol-3-yl)-4-[2-(4-methyl-piperazin-1-yl)-quinazolin-4-yl]-pyrrole-2,5-dione is readily soluble, preferably, in amounts of at least 10% by weight at 20° C., and a poor solvent in which it is more sparingly soluble, preferably in amounts of not more than about 0.1% by weight at 20° C., may also be employed provided that crystallization from the mixture at a reduced temperature of normally at least about 0° C., is possible using the selected solvent mixture.

It is preferred to add "seeds" of crystalline material to the solution in order to induce crystallization.

Furthermore, there is provided a process for the conversion of crystal form A to crystal form B, e.g. for preparing the form B from the form A.

In accordance with a preferred embodiment of the present invention, the crystalline forms of 3-(1.H.-indol-3-yl)-4-[2-(4-methyl-piperazin-1-yl)-quinazolin-4-yl]-pyrrole-2,5-dione acetate, e.g. the anhydrous forms, have a high crystallinity.

A crystal form is defined herein as having a "high crystallinity" or being "crystallographically pure" when it contains at most about 0.5% (w/w), e.g. at most about 0.1% (w/w) of other form. Thus e.g. "crystallographically pure Form A or B" contains about 0.5% (w/w) or less, e.g. about 0.1% (w/w) or less of another crystallographic form and/or amorphous form.

In one aspect the present invention provides pharmaceutical composition comprising an effective amount of the crystal of the invention, e.g. form A, form B or mixture thereof, preferably Form B in substantially pure form.

In a preferred embodiment, such a composition is a high dose formulation of including e.g. at least 50 mg, preferably at least 100 mg, more preferably at least 250 mg 3-(1.H.-indol-3-yl)-4-[2-(4-methyl-piperazin-1-yl)-quinazolin-4-yl]-pyrrole-2,5-dione acetate and a suitable pharmaceutical carrier or diluent. In another preferred example, such a composition is an oral formulation, comprising e.g. 0.5 mg to 2000 mg 3-(1.H.-indol-3-yl)-4-[2-(4-methyl-piperazin-1-yl)-quinazolin-4-yl]-pyrrole-2,5-dione acetate and a suitable pharmaceutical carrier or diluent.

The crystals of the invention are, therefore, useful in the treatment and/or prevention of diseases or disorders mediated by T lymphocytes and/or PKC, e.g. acute or chronic rejection of organ or tissue allo- or xenografts or T-cell mediated inflammatory or autoimmune diseases, e.g. atherosclerosis, vascular occlusion due to vacular injury such as angioplasty, restenosis, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock. The crystals of the invention are also useful in the treatment and/or prevention of T-cell mediated acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes type I or II and the disorders associated therewith, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis.

In accordance with the foregoing the present invention further provides:
  a pharmaceutical composition comprising the crystal of the invention, e.g. 3-(1.H.-indol-3-yl)-4-[2-(4-methyl-piperazin-1-yl)-quinazolin-4-yl]-pyrrole-2,5-dione acetate in amorphous form, crystalline form, e.g. Form A or Form B, or pseudocrystalline form, e.g. Form $S_A$ together with at least one pharmaceutically acceptable carrier or diluent;
  the crystals of the invention, e.g. 3-(1.H.-indol-3-yl)-4-[2-(4-methyl-piperazin-1-yl)-quinazolin-4-yl]-pyrrole-2,5-dione acetate in amorphous, crystalline or pseudocrystalline form, e.g. Form A, B, C, D or $S_A$, preferably Form A, B or mixture thereof for use as a pharmaceutical;
  the crystals of the invention, e.g. 3-(1.H.-indol-3-yl)-4-[2-(4-methyl-piperazin-1-yl)-quinazolin-4-yl]-pyrrole-2,5-dione acetate in amorphous, crystalline or pseudocrystalline form, e.g. Form A, B, C, D or $S_A$, preferably Form A, B or mixture thereof, for use in the preparation of a medicament;
  the crystals of the invention, e.g. 3-(1.H.-indol-3-yl)-4-[2-(4-methyl-piperazin-1-yl)-quinazolin-4-yl]-pyrrole-2,5-dione acetate in amorphous, crystalline or pseudocrystalline form, e.g. Form A, B, C, D or $S_A$ whenever prepared by a process as defined above;
  the use of the crystals of the invention, e.g. 3-(1.H.-indol-3-yl)-4-[2-(4-methyl-piperazin-1-yl)-quinazolin-4-yl]-pyrrole-2,5-dione acetate in amorphous, crystalline or pseudocrystalline form, e.g. Form A, B, C, D or $S_A$, in the preparation of a medicament for the treatment or prevention of diseases susceptible of therapy, such as diseases or disorders mediated by T lymphocytes and/or PKC, e.g. acute or chronic rejection of organ or tissue allo- or xenografts or T-cell mediated inflammatory or autoimmune diseases; and
  a method for the prevention or treatment of diseases or disorders mediated by T lymphocytes and/or PKC such as acute or chronic rejection of organ or tissue allo- or xenografts or T-cell mediated inflammatory or autoimmune diseases, comprising administration of a therapeutically effective amount of the crystals of the invention, e.g. 3-(1.H.-indol-3-yl)-4-[2-(4-methyl-piperazin-1-yl)-quinazolin-4-yl]-pyrrole-2,5-dione acetate in amorphous, crystalline or pseudocrystalline form, e.g. Form A, B or $S_A$, to a subject in need of such treatment.

The crystal of the invention, e.g. Form A or B, may be administered as the sole active ingredient or together with other drugs in immunomodulating regimens or other anti-inflammatory agents e.g. for the treatment or prevention of allo- or xenograft acute or chronic rejection or inflammatory or autoimmune disorders. For example, they may be used in combination with cyclosporines, or ascomycines or their immunosuppressive analogs or derivatives, e.g. cyclosporin A, cyclosporin G, FK-506, ABT-281, ASM 981; an mTOR inhibitor, e.g. rapamycin, 40-O-(2-hydroxy)ethyl-rapamycin etc.; corticosteroids; cyclophosphamide; azathioprene; methotrexate; an accelerating lymphocyte homing agent, e.g. FTY 720; leflunomide or analogs thereof; mizoribine; mycophenolic acid; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists. Crystalline form of the invention, e.g. Form A or B, may also be administered together with an antiproliferative drug, e.g. a chemotherapeutic drug, e.g. in cancer treatment, or with an anti-diabetic drug in diabetes therapy.

In accordance with the foregoing the present invention provides in a yet further aspect:
  A method as defined above comprising co-administration, e.g. concomitantly or in sequence, of a therapeutically effective amount of the crystal of the invention, e.g. 3-(1.H.-indol-3-yl)-4-[2-(4-methyl-piperazin-1-yl)-quinazolin-4-yl]-pyrrole-2,5-dione acetate in amorphous, crystalline or pseudocrystalline form, e.g. Form A, B, C, D or $S_A$, and a second drug substance, said second drug substance being an immunosuppressant, immunomodulatory, anti-inflammatory, antiproliferative or anti-diabetic drug, e.g. as indicated above.
  A therapeutic combination, e.g. a kit, comprising a) the crystal of the invention, e.g. 3-(1.H.-indol-3-yl)-4-[2-(4-methyl-piperazin-1-yl)-quinazolin-4-yl]-pyrrole-2,5-dione acetate in amorphous, crystalline or pseudocrystalline form, e.g. Form A, B, C, D or $S_A$, and b) at least one second agent selected from an immunosuppressant, immunomodulatory, anti-inflammatory, antiproliferative and anti-diabetic drug. Component a) and component b) may be used concomitantly or in sequence. The kit may comprise instructions for its administration.

A preferred crystalline form according to the invention is e.g. the Form B or A, more preferably the Form B.

The amorphous and crystalline forms of the present invention are synthesized in accordance with the following examples which are illustrative without limiting the scope of the present invention.

EXAMPLE 1

Preparation of Polymorph A

2-[2-(4-methyl-piperazin-1-yl)-quinazolin-4-yl]-acetamide (4.7 mg, 16.3 mmol) and 3-indoleglyoxylic acid methyl ester (4.35 mg, 1.3 eq.) are dissolved in THF (55 mL). To the suspension is added dropwise a 20% solution of t-BuOK in THF (46.5 g, 5.1 eq.) at −5° C. The mixture is stirred at 0-5° C. for 8 h and the conversion is checked by a PSC. After the conversion is complete, the reaction mixture is quenched with a mixture of 10% sodium chloride in water (50 ml) and acetic acid (5 g). Subsequent the aqueous layer is extracted with ethyl acetate (50 ml). The organic layer is extracted twice with 5% aqueous sodium bicarbonate (2×50 ml), followed by concentration to 40 ml residual volume. To the residue ethyl acetate (50 ml) is added and subsequently is distilled off. This procedure is carried out four times. To the distillation residue (40 ml) ethanol is added (30 ml). The red solution is heated to 70° C. over a period of 30 minutes and acetic acid (4 g) is added. After seeding the reaction is stirred at 70° C. for 90 minutes. The mixture is cooled to 30° C. over a period of 60 minutes and is stirred additionally for 30 minutes before it is cooled to 20° C. over a period of 90 minutes. After 14 h at 20° C. the suspension is filtered, washed once with TBME (15 ml) and once with a mixture TBME (13.5 ml)-ethanol (1.5 ml). After drying at 50° C. under reduced pressure for 2 h, the product is obtained in 87.7% yield as an orange crystalline solid.

$^1$H NMR (DMSO, 400 MHz) δ 1.92 (s, 3H), 2.13 (s, 3H), 2.17 (m, 4H), 2.51 (m, 1H), 3.69 (m, 4H), 6.35 (d, J=8.0 Hz, 1H), 6.64 (dd, J=7.8, 7.4 Hz, 1H), 7.02 (dd, J=7.6, 7.4 Hz, 1H), 7.10 (dd, J=7.8, 7.2 Hz, 1H), 7.38 (d, J=8.2 Hz, 1H), 7.53 (d, J=8.4 Hz, 1H), 7.63-7.73 (m, 2H), 8.13 (s, 1H), 11.29 (brs, 1H), 12.01 (brs, 1H).

EXAMPLE 2

Synthesis of Acetate Salt, Polymorph A:

40 mg of solid 3-(1.H.-indol-3-yl)-4-[2-(4-methyl-piperazin-1-yl)-quinazolin-4-yl]-pyrrole-2,5-dione are suspended in 0.75 ml of 2-propanol and the mixture is heated to 50° C. affording an almost clear solution. An equimolar amount of acetic acid is dissolved in 0.1 ml of 2-propanol and added drop-wise to the drug substance solution. The mixture is stirred at 50° C. for 1 to 2 hours and during this time the acetate salt precipitated out as a yellow powder. The suspension is cooled to ambient and the solid is recovered by vacuum filtration, followed by washing with small amounts of 2-propanol (2×0.25 ml).

EXAMPLE 3

Synthesis of Acetate Salt, Polymorph B:

220 mg of solid 3-(1. H.-indol-3-yl)-4-[2-(4-methyl-piperazin-1-yl)-quinazolin-4-yl]-pyrrole-2,5-dione were suspended in 2.5 ml of ethyl acetate and the suspension is heated to 50° C. producing an almost clear solution. An equimolar amount of acetic acid is dissolved in 0.25 ml of ethyl acetate and added drop-wise to the drug substance mixture. The mixture is stirred at 50° C. for 1 to 2 hours and during this time the acetate salt precipitated out as an orange powder. The suspension is cooled to ambient and the solid is recovered by vacuum filtration, followed by washing with small amounts of ethyl acetate (2×0.25 ml).

EXAMPLE 4

Conversion of Form A to Form B 25.0 g of solid -(1.H.-indol-3-yl)-4-[2-(4-methyl-piperazin-1-yl)-quinazolin-4-yl]-pyrrole-2,5-dione acetate salt form A are suspended in 200 ml of a 75/25 (vol/vol) ethyl acetate/ethanol mixture and heated up to 65° C. Addition of 30 ml of de-ionized water allows the dissolution of the solid and 100 ml of ethyl acetate are added at this temperature to yield a clear solution which is subsequently cooled down from 65° C. to 5° C. On cooling 50 ml of ethyl acetate are first added at 41° C. and further 50 ml of ethyl acetate at 14° C., the solution is seeded at this temperature with 0.5 g of solid -(1.H.-indol-3-yl)-4-[2-(4-methyl-piperazin-1-yl)-quinazolin-4-yl]-pyrrole-2,5-dione acetate salt form B. A thick orange suspension is obtained at 5° C. and kept under stirring at this temperature for 10 to 12 hours: The solid is recovered by filtration and the cake washed with 30 ml 75/25 (vol/vol) ethyl acetate/ethanol mixture. The orange powder is dried at 40° C. under vacuum (5 mbar) for 10 to 12 hours to yield 14.4 g of an orange solid exhibiting a XRD pattern which corresponds to that of polymorph B of -(1.H.-indol-3-yl)-4-[2-(4-methyl-piperazin-1-yl)-quinazolin-4-yl]-pyrrole-2,5-dione acetate salt.

EXAMPLE 5

Synthesis of acetate salt, polymorph C: 40 mg of solid AEB071 are suspended in 0.75 ml of methanol and the mixture is heated to 40° C. affording an almost clear solution. An equimolar amount of acetic acid is dissolved in 0.1 ml of methanol and added drop-wise to the drug substance solution. The reaction mixture is cooled to ambient and stirred overnight affording precipitation of the acetate salt as an orange powder. The suspension is cooled to ambient and the solid is recovered by vacuum filtration, followed by washing with small amounts of methanol (2×0.25 ml).

EXAMPLE 6

Synthesis of acetate salt, polymorph D: 40 mg of solid AEB071 are suspended in 0.75 ml of ethyl acetate and the mixture is heated to 40° C. affording an almost clear solution. An equimolar amount of acetic acid and 20 μLt of methanol (2.2% w with respect to ethyl acetate) are dissolved in 0.1 ml of ethyl acetate and added drop-wise to the drug substance solution. The reaction mixture is stirred at 40° C. for 1 to 2 hours affording precipitation of the acetate salt as an orange powder. The suspension is cooled to ambient and the solid is recovered by vacuum filtration, followed by washing with small amounts of ethyl acetate (2×0.25 ml).

EXAMPLE 7

Synthesis of acetate salt acetone solvate, polymorph $S_A$: 40 mg of solid 3-(1.H.-indol-3-yl)-4-[2-(4-methyl-piperazin-1-yl)-quinazolin-4-yl]-pyrrole-2,5-dione are suspended in 0.75 ml of acetone affording an almost clear solution at ambient. An equimolar amount of acetic acid is dissolved in 0.1 ml of acetone and added drop-wise to the drug substance solution. The reaction mixture is stirred at ambient for 1 to 2 hours affording precipitation of the acetate salt as an orange powder. The solid is recovered by vacuum filtration, followed by washing with small amounts of acetone (2×0.25 ml).

EXAMPLE 8

Synthesis of amorphous form: 4 g of solid 3-(1.H.-indol-3-yl)-4-[2-(4-methyl-piperazin-1-yl)-quinazolin-4-yl]-pyrrole-2,5-dione acetate in Form B are dissolved in 400 ml of acetone and spray-dried.

The invention claimed is:
1. Crystalline Form B of 3-(1.H.-indol-3-yl)-4-[2-(4-methyl-piperazin-1-yl)-quinazolin-4-yl]-pyrrole-2,5-dione acetate having an X-ray powder diffraction containing a diffraction peak at an angle of 9.7° 2theta.

2. The crystalline form according to claim 1 which is an anhydrate.

3. The crystalline form according to claim 1 exhibiting at least one of the following major IR bands 1754; 1711; 1486; 1462; 1378; 1248; 1086; 976; 770; 723; 661; 622 cm$^{-1}$.

4. The crystalline form according to claim 1 exhibiting at least one of the following main RAMAN bands: 3064; 1754; 1711; 1625; 1574; 1485, 1445; 1388; 1334; 1309; 1246; 1212; 664; 645 cm$^{-1}$.

5. The crystalline form according to claim 1 which is a solvate or hydrate.

6. The crystalline form according to claim 1 having a high crystallinity.

7. The crystalline form according to claim 1 in essentially pure form.

8. Processes for the preparation of the crystal form B according to claim 1 comprising forming a solution of 3-(1.H.-indol-3-yl)-4-[2-(4-methyl-piperazin-1;-yl)-quinazolin-4-yl]-pyrrole-2,5-dione acetate and crystallizing the acetate from solution by precipitation or recrystallization.

9. A crystalline form of 3-(1.H.-indol-3-yl)-4-[2-(4-methyl-piperazin-1-yl)-quinazolin-4-yl]-pyrrole-2,5-dione acetate according to claim 1 having an X-ray powder diffraction containing a diffraction peak at the following 2theta values: 8.4, 9.7, 13.9, 16.8, 17.3, 18.8, 19.0, 19.9, 20.5, 25.9, 27.1, 27.4, 27.8, 28.2, and 35.0.

* * * * *